United States Patent [19]

Uchida et al.

[11] Patent Number: 4,699,925
[45] Date of Patent: Oct. 13, 1987

[54] BIPHENYLYLPROPIONIC ACID DERIVATIVE AND PHARMACEUTICAL COMPOSITION CONTAINING THE SAME

[75] Inventors: Katsuhiro Uchida, Kyoto; Shozo Masumoto; Masao Tohno; Mitsuo Mimura; Makoto Okumura; Kiyonoshin Ichikawa; Misako Matsumura, all of Shiga, Japan

[73] Assignee: Kaken Pharmaceutical Co., Ltd., Tokyo, Japan

[21] Appl. No.: 531,535

[22] Filed: Sep. 12, 1983

[30] Foreign Application Priority Data

Sep. 10, 1982 [JP] Japan .................. 57-158578
Jun. 6, 1983 [JP] Japan .................. 58-101519

[51] Int. Cl.[4] .................. A61K 31/22; A61K 31/23; A61K 31/235; A01N 37/10
[52] U.S. Cl. .................. 514/559; 260/410.9 R; 260/410.5; 514/576; 560/102
[58] Field of Search .................. 560/102; 260/410.9 R; 514/559, 576

[56] References Cited

U.S. PATENT DOCUMENTS

| | | | |
|---|---|---|---|
| 2,518,922 | 8/1950 | Mowry. | |
| 3,752,844 | 8/1973 | Pfister | 560/10 |
| 3,755,427 | 8/1973 | Adams et al. | 560/102 X |
| 3,932,499 | 1/1976 | Adams et al. | 562/492 |
| 3,969,419 | 7/1976 | Enpl et al. | 560/102 X |
| 4,125,732 | 11/1978 | McEvoy et al. | 260/410.9 R X |
| 4,256,760 | 3/1981 | Los | 514/159 |
| 4,324,904 | 4/1982 | Hylton et al. | 560/102 |
| 4,433,160 | 2/1984 | Amano et al. | 560/102 X |
| 4,510,142 | 4/1985 | Cousse et al. | 560/102 X |
| 4,562,287 | 12/1985 | Vecchio et al. | 560/102 X |

Primary Examiner—Helen M. S. Sneed
Attorney, Agent, or Firm—Armstrong, Nikaido, Marmelstein & Kubovcik

[57] ABSTRACT

Biphenylylpropionic acid derivatives of the formula:

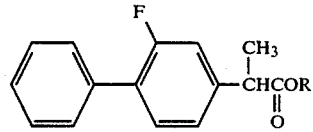

wherein R is an alkylcarbonyloxyalkyl group or an alkenylcarbonyloxyalkyl group having the formula:

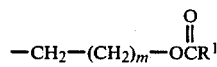

wherein $R^1$ is an alkyl group having 1 to 15 carbon atoms or an alkenyl group having 2 to 8 carbon atoms and m is 0 or an integer of 1. The compounds have excellent anti-inflammatory, analgesic and antipyretic activities. Moreover, the compounds have no irritation, rapid and long-acting, and high safety margin.

5 Claims, No Drawings

BIPHENYLYLPROPIONIC ACID DERIVATIVE AND PHARMACEUTICAL COMPOSITION CONTAINING THE SAME

BACKGROUND OF THE INVENTION

The present invention relates to novel biphenylylpropionic acid derivatives. More particularly, the present invention relates to biphenylylpropionic acid derivatives having the formula (I):

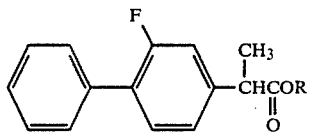

wherein R is an alkylcarbonyloxyalkyl group or an alkenylcarbonyloxyalkyl group having the formula (II):

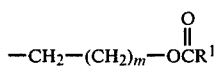

wherein $R^1$ is an alkyl group having 1 to 15 carbon atoms or an alkenyl group having 2 to 8 carbon atoms and m is 0 or an integer of 1, a process for preparing the same and a pharmaceutical composition containing the same as an effective ingredient.

It is known that 2-(2-fluoro-4-biphenylyl)propionic acid (hereinafter referred to as "FP") has strong anti-inflammatory, analgesic and antipyretic activities. However, the formulation form of FP is limited in the form of injection, syrup, or an external preparation such as ophthalmic agent, suppository, cream or plaster because of its irritation. Thus, various modifications are required for a pharmaceutical preparation of FP and the preparation is difficult.

As a result of various studies, the present inventors have now found that a satisfactory drug which has no irritation, an excellent pharmacological effect being several times higher than that of FP and less side effects. That is, the compound (I) of the present invention prepared from FP by esterifying has no irritation. Moreover, the compound (I) is excellent in absorption from mucosa or skin because of its high hydrophobic property. Thus, the pharmacological effect of the compound (I) is rapidly appeared and increased. On the other hand, when the compound (I) is formulated in combination with an oleaginous base, the pharmacological effect of the compound (I) is increased and prolonged, and the bioavailability of the compound (I) is increased. Further, the compound (I) is hard to bind with plasma proteins because of its physicochemical properties such as no free polar group and oil. As a result, the tissue distribution and metabolism of the compound (I) after administration are different from those of FP. Accordingly, the concentration of the compound (I) at an inflammatory site is increased to show an excellent pharmacological effects.

Therefore, the compound (I) of the present invention is excellent as a drug having no irritation, excellent pharmaceutical effects, rapid and long-acting, and a large safety margin.

It is an object of the present invention to provide novel FP ester derivatives which are useful and having excellent anti-inflammatory, analgesic and antipyretic activities, less side effects and high safety.

A further object of the invention is to provide a process for preparing FP ester derivatives.

Another object of the invention is to provide a pharmaceutical composition containing FP ester derivatives as effective ingredients.

These and other objects of the invention will become apparent from the description hereinafter.

SUMMARY OF THE INVENTION

In accordance with the present invention, there can be provided a FP ester derivative having the formula (I):

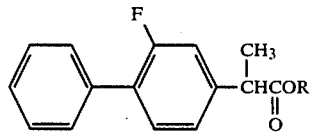

wherein R is an alkylcarbonyloxyalkyl group or an alkenylcarbonyloxyalkyl group having the formula (II):

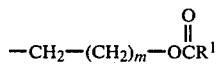

wherein $R^1$ is an alkyl group having 1 to 15 carbon atoms or an alkenyl group having 2 to 8 carbon atoms and m is 0 or an integer of 1.

DETAILED DESCRIPTION OF THE INVENTION

The preferable substituent group defined as R in the formula (I) is acetoxymethyl, propionyloxymethyl, isobutyryloxymethyl, pivaloyloxymethyl, palmitoyloxymethyl, crotonoyloxymethyl, 3,3-dimethylacryloyloxymethyl, 2-acetoxyethyl, 2-propionyloxyethyl, 2-crotonoyloxyethyl, 2-(3,3-dimethylacryloyloxy)ethyl, 2-(2,4-hexadienoyloxy)ethyl or 2-(3,7-dimethyl-2,6-octadienoyloxy)ethyl.

Representative compounds among the FP derivatives (I) are as follows:

Compound No. 1: acetoxymethyl 2-(2-fluoro-4-biphenylyl)propionate
Compound No. 2: propionyloxymethyl 2-(2-fluoro-4-biphenylyl)propionate
Compound No. 3: isobutyryloxymethyl 2-(2-fluoro-4-biphenylyl)propionate
Compound No. 4: crotonoyloxymethyl 2-(2-fluoro-4-biphenylyl)propionate
Compound No. 5: 3,3-dimethylacryloyloxymethyl 2-(2-fluoro-4-biphenylyl)propionate
Compound No. 6: palmitoyloxymethyl 2-(2-fluoro-4-biphenylyl)propionate
Compound No. 7: pivaloyloxymethyl 2-(2-fluoro-4-biphenylyl)propionate
Compound No. 8: 2-(acetoxy)ethyl 2-(2-fluoro-4-biphenylyl)propionate
Compound No. 9: 2-(propionyloxy)ethyl 2-(2-fluoro-4-biphenylyl)propionate
Compound No. 10: 2-(crotonoyloxy)ethyl 2-(2-fluoro-4-biphenylyl)propionate
Compound No. 11: 2-(3,3-dimethylacryloyloxy)ethyl 2-(2-fluoro-4-biphenylyl)propionate Compound No. 12: 2-(2,4-hexadienoyloxy)ethyl 2-(2-fluoro-4-biphenylyl)propionate Compound No. 13: 2-(3,7-dimethyl-2,6-octadienoyloxy)ethyl 2-(2-fluoro-4-biphenylyl)propionate The FP derivatives (I) of the present invention are prepared by reacting FP or the salt thereof having the formula (III):

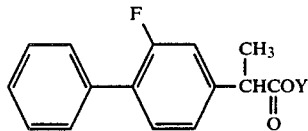  (III)

wherein Y is hydrogen atom or a metal salt, with a compound having the formula (IV):

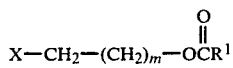  (IV)

wherein $R^1$ and m are as defined above and X is a halogen atom.

The FP derivatives having the formula (I) wherein m is 1 are also prepared by reacting 2-hydroxylethyl ester of FP having the formula (V):

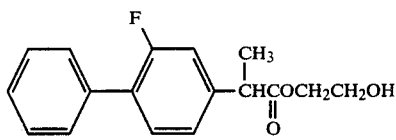  (V)

with an acid anhydride having the formula (VI):

  (VI)

wherein $R^2$ is a lower alkyl group having 1 to 2 carbon atoms or an alkenyl group having 2 to 7 carbon atoms, or by reacting a 2-haloethyl ester of FP having the formula (VII):

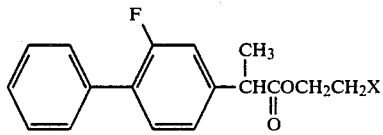  (VII)

wherein X is a halogen atom, with a compound having the formula (VIII):

  (VIII)

wherein $R^2$ is as defined above.

Though the above reactions can be conducted by employing any conventional esterifying reaction, the following method is preferred in point of yield and industrial production.

That is, the esterifying reactions of FP or the salt thereof having the formula (III) with the compound (IV), and the compound (VII) with the compound (VIII) are generally carried out in an aprotic organic solvent such as N,N-dimethylformamide, dimethylsulfoxide or hexamethylsulfonyltriamide, or an organic solvent such as acetonitrile, dichloromethane, dichloroethane, chloroform, benzene, ether or tetrahydrofuran, and in the presence or absence of an alkali metal carbonate such as sodium carbonate, potassium carbonate, sodium bicarbonate or potassium bicarbonate, an alkali hydroxide such as sodium hydroxide or potassium hydroxide, an alkali metal hydride such as sodium hydride, potassium hydride or lithium hydride, an organic base such as pyridine, triethylamine, N,N-dimethylaniline or tetramethylethylenediamine, an alkali metal iodide such as sodium iodide or potassium iodide, or a phase transfer catalyst such as a crown ether, e.g. 15-crown-5 or 18-crown-6, [2,2,2]-cryptand or [2,2,2]-benzocryptand.

Examples of the salt of the compound (III) employed in the above reaction are, for instance, metal salts such as silver and copper salt, alkali metal salts such as lithium, sodium and potassium salts. The above-mentioned aprotic solvents may be also employed in combination with ether, tetrahydrofuran, benzene, chloroform, dichloromethane, dichloroethane or acetone.

The amounts of the compounds (IV), (VI) and (VIII) to be used in the above reactions are usually employed in an amount not less than 1.0 mole, preferably 1.0 to 1.5 moles, per mole of the compound (III), (V) and (VII), respectively.

The reaction temperature is not particularly limited, but the reaction is usually carried out at a temperature of 0° to 120° C. Though the reaction time is varied depending on the reaction conditions such as kinds of solvent or catalyst and temperature, the reaction is usually carried out for several minutes to more then ten hours.

The FP derivatives (I) of the present invention have excellent anti-inflammatory, analgesic and antipyretic activities, and also a high degree of biological hydrolysis. Accordingly, the FP derivatives (I) are very useful as anti-inflammatory, analgesic, antipyretic and antirheumatoid agents. They can be formulated in a usual manner into compositions in the form of tablet, suppository, cream and capsule with conventional pharmaceutical carriers. Any conventional carriers used in preparations can be employed in the present invention. Examples of the carrier are, for instance, excipients, binders, lubricants, coloring agents, perfumes, emulsifying agents, dispersing agents, sterilized water, plant oil, harmless organic solvent, and the like.

With respect to the representative compounds of the present invention (the above-mentioned Compound Nos. 1 to 13), the values of $ED_{50}$ (50% effective dose) orally or intravenously in rats by a carrageenan-induced edema inhibitory test, $UD_{50}$ (50% ulcerative dose) orally in rats by a gastric irritation test, hydrolyzing rate in human plasma (incubation at 37° C. for one hour) and $LD_{50}$ (50% lethal dose) orally in mice are shown in Table 1.

TABLE 1

| Compound | $ED_{50}$ mg./kg. p.o. | $ED_{50}$ mg./kg. i.v. | $UD_{50}$ mg./kg. | Hydrolyzing rate (%) | $LD_{50}$ mg./kg. |
|---|---|---|---|---|---|
| Compounds of the intention | | | | | |
| 1 | 0.5 | 0.08 | 3.7 | 97.5 | 880 |
| 2 | 0.5 | 0.07 | 2.5 | 94.6 | 750 |
| 3 | 0.6 | 0.10 | 2.0 | 86.3 | 600 |
| 4 | 0.6 | 0.08 | 2.0 | 81.4 | 600 |
| 5 | 0.5 | 0.06 | 2.0 | 64.8 | 900 |
| 6 | 1.5 | 0.50 | 5.0 | 3.8 | 1000 |
| 7 | 0.6 | 0.10 | 2.5 | 70.3 | 840 |
| 8 | 0.7 | — | 2.0 | 100.9* | 650 |
| 9 | 0.7 | — | 2.0 | 98.9* | 700 |
| 10 | 0.9 | — | 3.0 | 99.5* | 800 |

TABLE 1-continued

| Compound | ED$_{50}$ mg./kg. p.o. | ED$_{50}$ mg./kg. i.v. | UD$_{50}$ mg./kg. | Hydrolyzing rate (%) | LD$_{50}$ mg./kg. |
|---|---|---|---|---|---|
| 11 | 1.0 | — | 3.0 | 99.8* | 880 |
| 12 | 0.9 | — | 3.0 | 100.3* | 750 |
| 13 | 0.9 | — | 3.0 | 101.0* | 750 |
| Comparative compounds | | | | | |
| acemethacin | 8.3 | — | 17.5 | 4.2 | 18.0 |
| indomethacin | 5.5 | 1.25 | 5.0 | — | 14.0 |
| FP | 0.8 | 0.3 | 1.0 | — | 440 |

*Values in rat plasma

As is clear from Table 1, the compounds (I) of the present invention have excellent pharmacological effects in comparison with the comparative compounds such as acemethacin, indomethacin and FP. For example, the carrageenan-induced edema inhibitory effect of the compound (I) is about 8 times that of indomethacin and the same as that of FP. With respect to ulceration of gastrointestinal tract which is one of the main side effects of anti-inflammatory agents, the ulcerative effect of the compound (I) is about one third that of FP. LD$_{50}$ of the compound (I) is 1.5 to 2.0 times higher than that of FP. Thus, the acute toxicity of the compound (I) is considerably reduced. Furthermore, the safety margin of the compound (I) expressed by a ratio of UD$_{50}$ to ED$_{50}$ is about 3 times broader than that of FP.

The present invention is more particularly described and explained by means of the following Examples, in which all % are by weight unless otherwise noted. In order to illustrate the preparation of (2-hydroxyethyl) 2-(2-fluoro-4-biphenylyl)propionate and (2-bromoethyl) 2-(2-fluoro-4-biphenylyl)propionate employed as starting materials for preparing the FP derivatives (I) of the invention, the following Reference Examples are also presented.

REFERENCE EXAMPLE 1

[(2-Hydroxyethyl) 2-(2-fluoro-4-biphenylyl)propionate]

In 45 ml. of anhydrous dimethylformamide (hereinafter referred to as "DMF") was dissolved 12.2 g. (50 mmoles) of FP. To the resulting solution was added 6.9 g. (50 mmoles) of anhydrous potassium carbonate. After adding dropwise 6.25 g. (50 mmoles) of ethylene bromohydrin with ice-cooling, the reaction was carried out at 60° to 70° C. for 15 hours with stirring. After cooling the reaction mixture with ice, the resulting inorganic material was filtered off, and then the solvent was distilled away under reduced pressure. To the resulting residue was added 50 ml. of diethyl ether, and then the resulting mixture was washed successively with water, 10% solium carbonate solution and a saturated sodium chloride solution, and the organic lawer was dried with magnesium sulfate. The solvent was distilled away under reduced pressure to give 13.8 g. of clear oily material. The resulting oily material was further purified by chromatography of silica gel (Kiesel gel 60 F made by Merck & Co., Inc.; Developing solvent: (1) dichloromethane (2) dichloromethane:ether=9:1 (3) dichloromethane:ether=8:2) to give 9.97 g. (yield: 69.2%) of white crystal of the desired compound having a melting point of 73° to 75° C.

Mass spectrum (20 eV, Direct) m/e: 288 (M+), 244, 199 (base peak), 184, 178 and 45.

REFERENCE EXAMPLE 2

[(2-Bromoethyl) 2-(2-fluoro-4-biphenylyl)propionate]

In 40 ml. of dichloromethane was dissolved 12.2 g. (50 mmoles) of FP. To the resulting solution were added 6.25 g. (50 mmoles) of ethylene bromohydrin and 0.3 g. (2.5 mmoles) of p-dimethylaminopyridine. After adding dropwise 10.3 g. (50 mmoles) of dicyclohexylcarbodiimide dissolved in dichloromethane, the reaction was carried out at a room temperature for 30 minutes with stirring. After cooling the reaction mixture with ice, the insoluble material was filtered off, and then the organic layer was washed successively with 0.1N hydrochloride, saturated sodium hydrogencarbonate solution and saturated sodium chloride solution, and dried with anhydrous magnesium sulfate. After distilling away the solvent under reduced pressure, the precipitated dicyclohexylurea was filtered off. The resulting yellowish oily material was purified in the same manner as in Reference Example 1 to give 15.6 g. (yield: 89%) of the desired compound being a clear oily material.

Mass spectrum (20 eV, Direct) m/e: 351 (M+), 353 (M+2), 244, 199 (base peak), 184, 178, 108 and 110.

EXAMPLE 1

[Acetoxymethyl 2-(2-fluoro-4-bipenylyl)propionate (Compound No. 1)]

In 100 ml. of anhydrous DMF was dissolved 7.32 g. (30 mmoles) of FP. To the resulting solution was added 2.1 g. (15 mmoles) of anhydrous potassium carbonate with ice-cooling, and then the resulting mixture was stirred for one hour. After adding dropwise 3.3 g. (30 mmoles) of acetoxymethyl chloride purified by distillation at 0° to 5° C. for 10 minutes, the reaction was carried out with stirring at a room temperature for 2 hours. After cooling the resulting reaction mixture with ice and filtering off the inorganic materials, the solvent was distilled away under reduced pressure. To the obtained residue was added 150 ml. of diethyl ether, and then the residue was washed successively with water, 10% of sodium carbonate solution and a saturated sodium chloride solution. The obtained organic layer was dried with anhydrous magnesium sulfate, and then the solvent was distilled away under reduced pressure to give 8.24 g. (yield: 86.9%) of the desired compound being an oily material.

The product was further distilled under reduced pressure in an atmosphere of nitrogen gas to give 6.55 g. (yield: 69.1%) of an oily material having a boiling point of 195° to 197° C./0.4 mmHg.

Elementary analysis for $C_{18}H_{17}C_4F$ (MW: 316): Calcd.(%): C, 68.35; H, 5.38; Found (%): C, 68.42; H, 5.51.

Nuclear magnetic resonance spectrum (in CCl$_4$, TMS), δ(ppm): 1.49 (d, 3H, >CH—CH$_3$), 2.00 (s, 3H, —OCO—CH$_3$), 3.74 (q, 1H, CH$_3$—CH<), 5.71 (s, 2H, —O—CH$_2$—O—), 7.03 to 7.56 (m, 8$\overline{\text{H}}$, aromatic H)

Mass spectrum (20 eV, Direct) m/e: 316 (M.+), 226 ([M—OCH$_2$OAc]+), 199 (base peak, [M—CO$_2$CH$_2$OAc]+), 73 [—CH$_2$OAc]+ and 43 [—COCH$_3$]+

Infrared absorption spectrum (ν cm.$^{-1}$): 3100 to 2850 (aromatic alkyl ν C—H), 1760 (ν COOR), 1625 to 1420 (aromatic, ν C=C) and 1370 (ν COCH$_3$)

Refractive index: n$_D^{26}$=1.5488

Ultraviolet absorption: λmax=248 nm.

EXAMPLE 2

[Propionyloxymethyl 2-(2-fluoro-4-biphenylyl)propionate (Compound No. 2)]

In 100 ml. of anhydrous DMF was dissolved 7.32 g. (30 mmoles) of FP. To the resulting solution was added 2.1 g. (15 mmoles) of anhydrous potassium carbonate with ice-cooling, and then the reaction mixture was stirred for one hour. After adding dropwise 4.78 g. (39 mmoles) of propionyloxymethyl chloride purified by distillation with ice-cooling, the reaction was carried out with stirring at a room temperature for 2 hours, and then at 60° to 70° C. for one hour. After completion of the reaction, the reaction mixture was cooled, and then the inorganic material was filtered off. After distilling away the solvent under reduced pressure, 150 ml. of dimethyl ether was added to the residue, and then the organic layer was washed successively with water, 10% sodium carbonate solution and a saturated sodium chloride solution. After drying the obtained organic layer with anhydrous magnesium sulfate, the solvent was distilled away under reduced pressure. The resulting product was further distilled under reduced pressure in an atmosphere of nitrogen gas to give 7.35 g. (yield: 74.2%) of the desired compound being a colorless oily material having a boiling point of 195° to 196° C./0.8 mmHg.

Elementary analysis for $C_{19}H_{19}O_4F$ (MW: 330): Calcd.(%): C, 69.09; H, 5.76; Found (%): C, 69.33; H, 5.98.

Nuclear magnetic resonane spectrum (in $CCl_4$, TMS), δ(ppm): 1.08 (t, 3H, —$CH_2$—$CH_3$), 1.52 (d, 3H, $CH_3$—CH), 2.26 (q, 2H, —$CH_2$—$CH_3$), 3.72(q, 1H, $CH_3$—CH<), 5.69 (s, 2H, —O—$CH_2$—O—) and 7.06 to 7.55 (m, 8H, aromatic H)

Mass spectrum (20 eV, Diret) m/e:

330 (M$\overset{+}{\cdot}$), 226 ([M—OCH$_2$OCEt]$^+$), 199

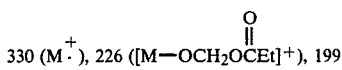

([M—CO$_2$CH$_2$OCEt]$^+$), 87 ([—CH$_2$—OCEt]$^+$) and

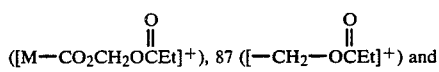

57 (base peak, [—CEt]$^+$)

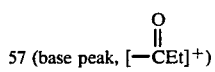

Infrared absorption spectrum ($\nu$ cm.$^{-1}$): 3100 to 2850 (aromatic, alkyl$\nu$ C—H), 1760 ($\nu$COO—R) and 1625 to 1420 (aromatic$\nu$ C=C)

Refractive index: $n_D^{26}$ = 1.5431

Ultraviolet absorption: λmax = 248 nm.

EXAMPLE 3

[Isobutyryloxymethyl 2-(2-fluoro-4-biphenylyl)propionate (Compound No. 3)]

The procedure of Example 2 was repeated except that 4.08 g. (30 mmoles) of isobutylyloxymethyl chloride was employed instead of propionyloxymethyl chloride, to give 7.29 g. (yield: 70.6%) of the desired compound being an oily material having a boiling point of 188° to 190° C./0.4 mmHg.

Elementary analysis for $C_{20}H_{21}O_4F$ (MW: 344) Calcd.(%): C, 69.77; H, 6.10; Found (%): C, 70.03; H, 6.08.

Nuclear magnetic resonance spectrum (in $CCl_4$, TMS), δ(ppm):

0.98 to 1.20 (m, 6H, —CH<$^{CH_3}_{CH_3}$, 1.50 (d, 3H, 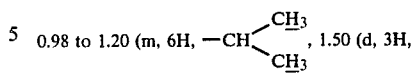

$CH_3$—CH<), 2.46 (m, 1H, —CH<$^{CH_3}_{CH_3}$, 3.72 (q, 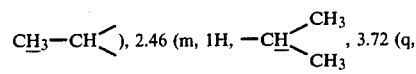

1H, $CH_3$—CH<), 5.69 (s, 2H, —O—$CH_2$—O—) and 7.00 to 7.60 (m, 8H, aromatic H)

Mass spectrum (20 eV, Direct) m/e:

344 (M$\overset{+}{\cdot}$), 243 ([M—CH$_2$OCCH(CH$_3$)$_2$]$^+$),

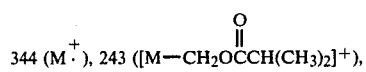

226 ([M—OCH$_2$OCCH(CH$_3$)$_2$]$^+$), 199 (base peak,

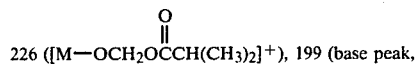

[M—CO$_2$CH$_2$OCCH(CH$_3$)$_2$]$^+$), 101

([—CH$_2$OCCH(CH$_3$)$_2$]$^+$), 71 ([—COCH(CH$_3$)$_2$]$^+$) and

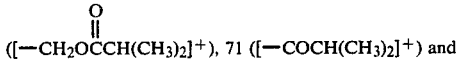

43 ([—CH(CH$_3$)$_2$]$^+$)

Infrared absorption spectrum ($\nu$ cm.$^{-1}$): 3100 to 2850 (aromatic, alkyl $\nu$ C—H), 1755 ($\nu$COO—R) and 1625 to 1420 (aromatic $\nu$ C=C)

Refractive index: $n_D^{26}$ = 1.5409

EXAMPLE 4

[Crotonoyloxymethyl 2-(2-fluoro-4-biphenylyl)propionate (Compound No. 4)]

The procedure of Example 2 was repeated except that 4 g. (30 m moles) of crotonoyloxymethyl chloride instead of propionyloxymethyl chloride was employed, to give 5.57 g. (yield: 54.3%) of the desired compound being an oily material having a boiling point of 217° to 219° C./0.4 mmHg.

Elementary analysis for $C_{20}H_{19}O_4F$ (MW: 342) Calcd.(%): C, 70.18; H, 5.55; Found (%): C, 70.46; H, 5.79.

Nuclear magnetic resonance spectrum (in $CCl_4$, TMS), δ (ppm): 1.52 (d, 3H, $CH_3$—CH<), 1.68 to 1.95 (m, 3H, olefinic $CH_3$), 3.73 (q, 1H, $CH_3$—CH<), 5.67 to 5.94 (m, 1H, olefinic H), 5.75 (s, 2H, —O—$CH_2$—O—), 6.80 to 6.98 (m, 1H, olefinic H) and 7.00 to 7.52 (m, 8H, aromatic H)

Mass spectrum (20 eV, Direct) m/e:

342 (M$^+$), 226 ([M—OCH$_2$OCCH=CHCH$_3$]$^+$),

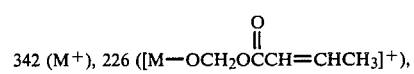

199 ([M—CO$_2$CH$_2$OCCH=CHCH$_3$]$^+$) and

69 (base peak, [—COCH=CHCH$_3$]$^+$)

Infrared absorption spectrum ($\nu$ cm.$^{-1}$): 3100 to 2850 (aromatic, alkyl $\nu$ C—H), 1740 ($\nu$COO—R) and 1658

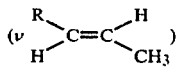

Refractive index: $n_D^{26} = 1.5525$
Ultraviolet absorption: $\lambda max = 248$ nm.

EXAMPLE 5

[3,3-Dimethylacryloyloxymethyl 2-(2-fluoro-4-biphenylyl)propionate (Compound No. 5)]

The procedure of Example 2 was repeated except that 5.8 g. (39 mmoles) of 3,3-dimethylacryloyloxymethyl chloride instead of propionyloxymethyl chloride was employed, to give 6.57 g. (yield: 61.5%) of the desired compound being an oily material having a boiling point of 210° to 214° C./0.5 mmHg.

Elementary analysis for $C_{21}H_{21}O_4F$ (MW: 356): Calcd.(%): C, 70.79; H, 5.90; Found (%): C, 71.12; H, 6.25.

Nuclear magnetic resonance spectrum (in CCl$_4$, TMS), $\delta$ (ppm): 1.52 (d, 3H, CH$_3$—CH<), 1.94 (s, 3H, olefinic CH$_3$), 2.10 (s, 3H, olefinic CH$_3$), 3.70 (q, 1H, CH$_3$—CH<), 5.55 to 5.69 (m, 1H, olefinic H), 5.72 (s, 2H, —O—CH$_2$—O—) and 7.00 to 7.51 (m, 8H, aromatic H).

Mass spectrum (20 eV, Direct) m/e:

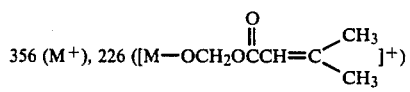

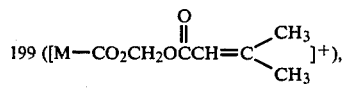

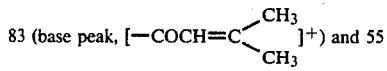

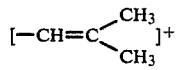

Infrared absorption spectrum ($\nu$ cm.$^{-1}$): 3100 to 2850 (aromatic, alkyl $\nu$ C—H), 1745 ($\nu$COO—R), 1645

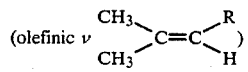

and 1625 to 1420 (aromatic $\nu$C=C)
Refractive index: $n_D^{26} = 1.5535$.

EXAMPLE 6

[Palmitoyloxymethyl 2-(2-fluoro-4-biphenylyl)propionate (Compound No. 6)]

The procedure of Example 2 was repeated except that an ether solution of 11.9 g. (39 mmoles) of palmitoyloxymethyl chloride instead of propionyloxymethyl chloride was employed, to give 9.7 g. (yield: 73.1%) of white crystals of the crude desired compound. The resulting product was purified by centrifugal liquid chromatography (carrier: KT 2106 made by Fuji gel Co., Ltd.; Eluent: cyclohexane:dichloromethane=1:1) to give 7.3 g. (yield: 47.5%) of white crystals of the desired compound having a melting point of 45.5° to 48° C.

Elementary analysis for $C_{32}H_{45}O_4F$ (MW: 512): Calcd.(%): C, 75.0; H, 8.79; Found (%): C, 75.34; H, 9.04.

Nuclear magnetic resonance spectrum (in CCl$_4$, (TMS), $\delta$ (ppm): 0.88 (t, 3H, —CH$_2$—CH$_3$), 1.11 to 1.42 (m, 26H, alkyl H), 1.51 (d, 3H, CH$_3$—CH<), 2.23 (t, 2H, —OCO—CH$_2$—CH$_2$—), 3.71 (q, 1H, CH$_3$—CH<), 5.65 (s, 2H, —O—CH$_2$—O—) and 7.00 to 7.67 (m, 8H, aromatic H)

Mass spectrum (20 eV, Direct) m/e:

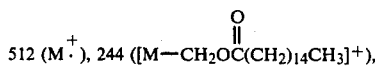

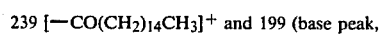

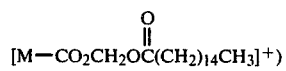

Infrared absorption spectrum ($\nu$ cm.$^{-1}$): 3100 to 2800 (aromatic, alkyl $\nu$ C—H), 1755 ($\nu$COO—R) and 1625 to 1420 (aromatic $\nu$C=C)

EXAMPLE 7

[Pivaloyloxymethyl 2-(2-fluoro-4-biphenylyl)propionate (Compound No. 7)]

The procedure of Example 2 was repeated except that 4.51 g. (30 mmoles) of pivaloyloxymethyl chloride instead of propionyloxymethyl chloride was employed to give 7.73 g. (yield: 72.0%) of the desired compound being an oily material having a boiling point of 191° to 194° C./0.4 mmHg.

Elementary analysis for $C_{21}H_{23}FO_4$ (MW: 358): Calcd.(%): C, 70.45; H, 6.49; Found (%): C, 69.73; H, 6.88.

Nuclear magnetic resonance spectrum (in CCl$_4$, TMS), $\delta$ (ppm): 1.10 (s, 9H, —C(CH$_3$)$_3$), 1.50 (d, 3H, CH$_3$—CH<), 3.72 (q, 1H, CH$_3$—CH<), 5.69 (s, 2H, —O—CH$_2$—O—) and 7.00 to 7.60 (m, 8H, aromatic H).

Mass spectrum (20 eV, Direct) m/e:

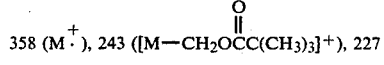

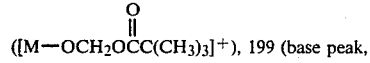

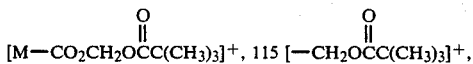

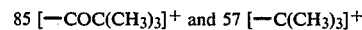

Infrared absorption spectrum ($\nu$ cm.$^{-1}$): 3100 to 2850 (aromatic, alkyl $\nu$ C—H), 1755 ($\nu$ COOR) and 1625–1420 (aromatic $\nu$ C=C)
Refractive index: $n_D^{26} = 1.5398$
Ultraviolet absorption: $\lambda max = 248$ nm.

EXAMPLE 8

[Acetoxymethyl 2-(2-fluoro-4-biphenylyl)propionate (Compound No. 1)]

In 150 ml. of anhydrous DMF was dissolved 2.8 g. of potassium salt of FP. To the resulting solution was added 1.2 g. of acetoxymethyl chloride, and the reaction mixture was stirred at a room temperature for one hour. The resulting reaction mixture was treated and purified in the same manner as in Example 1 to give 2.56 g. (yield: 81%) of the desired compound. The physicochemical properties of the obtained compound were consistent with those obtained in Example 1.

EXAMPLE 9

[2-(Acetoxy)ethyl 2-(2-fluoro-4-biphenylyl)propionate (Compound No. 8)]

In 25 ml. of anhydrous dichloromethane was dissolved 2.44 g. (10 mmoles) of FP. To the resulting solution were added 1.04 g. (10 mmoles) of (2-acetoxy)ethyl alcohol and 0.13 g. (1 mmole) of p-dimethylaminopyridine with stirring at 0° C. After adding dropwise 2.3 g. (11 mmoles) of dicyclohexylcarbodiimide dissolved in anhydrous dichloromethane, the reaction was carried out at a room temperature for one hour. After ice-cooling, the insoluble material was filtered off, and then the organic layer was washed successively with 0.1N hydrochloride, a saturated sodium hydrogencarbonate solution and a saturated sodium chloride solution, and dried with anhydrous magnesium sulfate. After distilling away the solvent under reduced pressure, the resulting clear oily material was distilled under reduced pressure for purification. The fractions of distillate having a boiling point of 234° to 238° C./mmHg were collected to give 2.6 g. (yield: 80%) of the desired compound being a clear oily material.

Elementary analysis for $C_{19}H_{19}FO_4$ (MW: 330.4): Calcd.(%): C, 69.07; H, 5.75; Found (%): C, 69.28; H, 5.77.

Nuclear magnetic resonance spectrum (in $CCl_4$, TMS), δ(ppm):

1.55 (d, 3H, CH—CH$_3$), 1.96 (s, 3H, —OCCH$_3$),

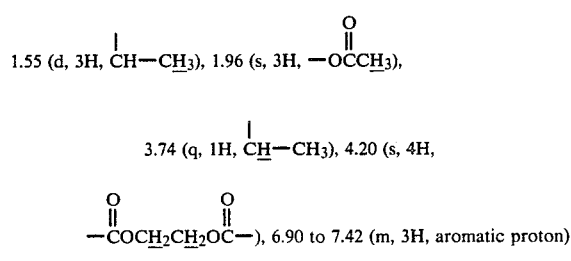

—COCH$_2$CH$_2$OC—), 6.90 to 7.42 (m, 3H, aromatic proton)

Mass spectrum (20 eV, Direct) m/e:

330 (M$^+$), 226, 199 [base peak,

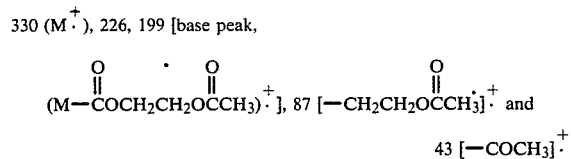

(M—COCH$_2$CH$_2$OCCH$_3$)$^+$], 87 [—CH$_2$CH$_2$OCCH$_3$]$^+$ and

43 [—COCH$_3$]$^+$

Infrared absorption spectrum (νcm.$^{-1}$): 3100 to 2850 (aromatic, alkyl νC—H), 1760 (ester νC=O), 1625 to 1420 (aromatic νC=C)

Refractive index: $n_D^{27} = 1.5427$

EXAMPLE 10

[2-(Propionyloxy)ethyl 2-(2-fluoro-4-biphenylyl)propionate (Compound No. 9)]

In 25 ml. of anhydrous DMF was dissolved 2.44 g. (10 mmoles) of FP. To the resulting solution was added 1.38 g. (10 mmoles) of anhydrous potassium carbonate, and the reaction mixture was stirred at a room temperature for one hour. After adding dropwise 1.77 g. (13 mmoles) of (2-propionyloxy)ethyl chloride, the reaction was carried out at 40° to 50° C. for one hour with stirring. After ice-cooling, the inorganic material was filtered off, and then the solvent was distilled away under reduced pressure. After adding 50 ml. of diethyl ether to the resulting residue, the mixture was washed successively with water, 10% sodium carbonate solution and a saturated sodium chloride solution, and then the organic layer was dried with anhydrous magnesium sulfate. After distilling away the solvent under reduced pressure, the resulting clear oily material was distilled under reduced pressure for purification. The fractions of distillate having a boiling point of 225° to 228° C./0.5 mmHg were collected to give 2.55 g. (yield: 74%) of the desired compound being a clear oily material.

Elementary analysis for $C_{20}H_{21}FO_4$ (MW: 344.4): Calcd.(%): C, 69.69; H, 6.10; Found (%): C, 69.90; H, 6.12.

Nuclear magnetic spectrum (in $CCl_4$, TMS), δ(ppm):

1.08 (t, 3H, —CH$_2$CH$_3$), 1.52 (d, 3H, —CH—CH$_3$), 2.26 (q, 2H, —CH$_2$CH$_3$), 2.75 (q, 1H, —CH—CH$_3$),

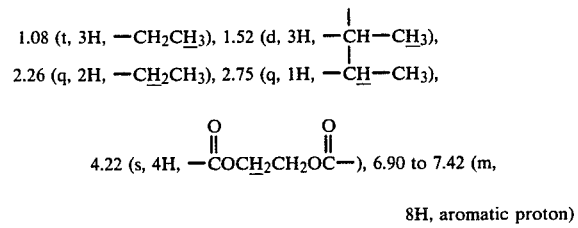

4.22 (s, 4H, —COCH$_2$CH$_2$OC—), 6.90 to 7.42 (m, 8H, aromatic proton)

Mass spectrum (20 eV, Direct) m/e:

344 (M$^+$), 226, 199 [base peak

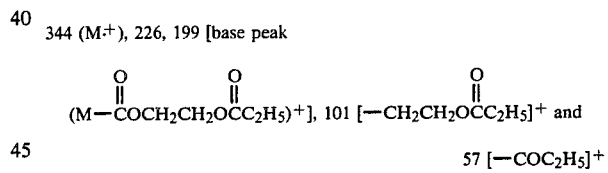

(M—COCH$_2$CH$_2$OCC$_2$H$_5$)$^+$], 101 [—CH$_2$CH$_2$OCC$_2$H$_5$]$^+$ and

57 [—COC$_2$H$_5$]$^+$

Infrared absorption spectrum (νcm.$^{-1}$): 3100 to 2850 (aromatic alkyl νC—H), 1760 (ester νC=O), 1625 to 1420 (aromatic νC=C)

Refractive index: $n_D^{27} = 1.5397$

EXAMPLE 11

[2-(Crotonoyloxy)ethyl 2-(2-fluoro-4-biphenyl)propionate (Compound No. 10)]

The procedure of Example 10 was repeated except that 2.89 g. (15 mmoles) of (2-crotonoyloxy)ethyl bromide instead of (2-propionyloxy)ethyl chloride was employed to give 3.39 g. (yield: 63.4%) of the desired compound being a clear oily material having a boiling point of 205° to 215° C./1.5 mmHg.

Elementary analysis for $C_{21}H_{21}FO_4$ (MW: 356.4): Calcd.(%): C, 70.77; H, 5.89; Found (%): C, 70.98; H, 5.91.

Nuclear magnetic resonance (in $CCl_4$, TMS), δ(ppm): 1.40 (d, 3H, —CH—CH$_3$), 1.72 (dd, 3H, olefinic —CH$_3$), 3.57

(q, 1H, —C<u>H</u>—CH₃), 4.06 (s, 4H, —COC<u>H</u>₂C<u>H</u>₂OC—), 5.54, 5.51 (dd, 3H, olefinic proton), 6.44 to 7.33 (m, 9H, aromatic olefinic proton)

Mass spectrum (20 eV, Direct) m/e:

356 (M·⁺), 226, 199 [base peak, (M—COCH₂CH₂OCCH=CHCH₃)⁺], 113

[—CH₂CH₂OCCH=CHCH₃]⁺, 69 [—COCH=CHCH₃]⁺

Infrared absorption spectrum (νcm.⁻¹): 3100 to 2850 (aromatic alkyl νC—H), 1720 to 1750 (ester νC=O), 1665 (olefinic νC=C)

Refractive index: $n_D^{27}$=1.5461

EXAMPLE 12

[2-(3,3-Dimethylacryloyloxy)ethyl 2-(2-fluoro-4-biphenylyl)propionate (Compound No. 11)]

The procedure of Example 10 was repeated except that 3.10 g. (15 mmoles) of 2-(3,3-dimethylacryloyloxy)ethylbromide instead of (2-propionyloxy)ethyl chloride, was employed to give 3.31 g. (yield: 59.6%) of the desired compound being a clear oily material having a boiling point of 225° to 228° C./0.8 mmHg.

Elementary analysis for C₂₂H₂₃FO₄ (MW: 370.5): Calcd.(%): C, 71.32; H, 6.21; Found (%): C, 71.53; H, 6.24.

Nuclear magnetic resonance spectrum (in CCl₄, TMS), δ(ppm):

1.44 (d, 3H, —C<u>H</u>—CH₃), 1.72 (s, 3H, olefinic

—CH₃), 2.03 (s, 3H, olefinic —C<u>H</u>₃), 3.62 (q,

1H, —C<u>H</u>—CH₃), 4.08 (s, 4H—COC<u>H</u>₂CH₂OC—), 5.40 (m, 1H, olefinic proton) and 6.82 l to 7.52 (m, 8H, aromatic proton).

Mass spectrum (20 eV, Direct) m/e:

370 (M·⁺), 226, 199 [base peak,

[M—COCH₂CH₂OCCH=C(CH₃)₂]⁺], 127

[—CH₂CH₂OCCH=C(CH₃)₂]⁺, 83 [—COCH=C(CH₃)₂]⁺ and

55 [—CH=C(CH₃)₂]⁺

Infrared absorption spectrum (νcm.⁻¹): 3100 to 2850 (aromatic alkyl νC—H), 1745, 1725 (ester νC=O) and 1655

Refractive index: $n_D^{27}$=1.5431

EXAMPLE 13

[2-(3,7-Dimethyl-2,6-octadienoyloxy)ethyl 2-(2-fluoro-4-biphenylyl)propionate (Compound No. 13)]

The procedure of Example 10 was repeated except that 1.68 g. (10 mmoles) of 3,7-dimethyl-2,6-octadienoic acid, 10 ml. of anhydrous DMF, 1.38 g. (10 mmoles) of anhydrous potassium carbonate and 3.51 g. (10 mmoles) of 2-bromoethyl 2-(2-fluoro-4-biphenylyl)propionate were employed. The resulting residue was purified by chromatography of silica gel (Kiesel gel 70 F (90 g.); Developing solvent: a mixed solvent of dichloromethane and cyclohexane) to give 3.1 g. (yield: 83.7%) of the desired compound being a clear oily material having a boiling point of not less than 250° C./mmHg.

Elementary analysis for C₂₇H₃₁FO₄ (MW: 438.6): Calcd.(%): C, 73.94; H, 7.07; Found (%): C, 74.16; H, 7.06.

Nuclear magnetic resonance spectrum (in CCl₄, TMS), δ(ppm):

1.44 (d, sH, Ph—C<u>H</u>—C<u>H</u>₃), 1.46, 1.55 (ss, 6H, olefinic —CH₃ × 2), 1.96 (m, 7H, olefinic —C<u>H</u>₃, olefinic —C<u>H</u>₂—C<u>H</u>₂—), 3.96 (s, 4H,

—CO—CH₂CH₂—OC—), 4.66 to 4.92 (m, 1H, olefinic proton), 5.24 (s, 1H, olefinic proton) and 6.64 to 7.18 (m, 3H, aromatic proton)

Mass spectrum (20 eV, Direct) m/e:

438 (M·⁺), 226, 199 [base peak

[M—COCH₂CH₂OCCH=C—CH₂CH₂CH=C(CH₃)₂]⁺],

195 [—CH₂CH₂OCCH=C(CH₃)CH₂CH₂CH=C(CH₃)₂]⁺,

151 [—COCH=C(CH₃)CH₂CH₂CH=C(CH₃)₂]⁺ and

69 [—CH₂CH=C(CH₃)₂]⁺

Infrared absorption spectrum (νcm.⁻¹): 3100 to 2850 (aromatic alkyl νC—H), 1745, 1730 (ester νC=O) and 1650 (olefinic νC=C)

Refractive index: $n_D^{27}$=1.5435

EXAMPLE 14

[2-(2,4-Hexadienoyloxy)ethyl 2-(2-fluoro-4-biphenylyl)-propionate (Compound No. 12)]

To 200 ml. of anhydrous acetonitrile were added 0.1 g. of 18-crown-6, 1.5 g. (20 mmoles) of potassium sorbate and 3.5 g. (10 mmoles) of (2-bromoethyl) 2-(2-fluoro-4-biphenylyl)propionate, and then the resulting reaction mixture was stirred at 50° C. for 8 hours. The resulting reaction mixture was treated and purified by conventional methods in the same manner as in Example 27 to give 3.5 g. (yield: 91.6%) of the desired compound being a white crystal having a melting point of 59° to 61° C.

Elementary analysis for $C_{23}H_{23}FO_4$ (MV: 382.3): Calcd.(%): C, 72.26; H, 6.02, Found (%): C, 72.40; H, 6.04.

Nuclear magnetic resonance spectrum (in $CCl_4$, TMS), δ(ppm):

1.44 (d, 3H, Ph—CH(|)—C$\underline{H}_3$), 1.71 (d, 3H, olefinic

—$CH_3$), 3.48 (q, 1H, Ph—C$\underline{H}$—$CH_3$), 4.00 (s, 4H,

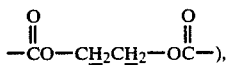

proton), 5.63 to 5.72 (m, 2H, olefinic proton) and 6.60 to 7.18 (m, 9H, aromatic, olefinic proton)

Mass spectrum (20 eV, Direct) m/e:

382 (M$\overset{+}{\cdot}$), 271 [M—O$\overset{O}{\overset{\|}{C}}$CH=CH—CH=CHCH$_3$]$^+$, 226 (base peak), 199 [M—$\overset{O}{\overset{\|}{C}}$OCH$_2$CH$_2$O$\overset{O}{\overset{\|}{C}}$CH=CH—CH=CHCH$_3$]$^+$, 139 [—CH$_2$CH$_2$O$\overset{O}{\overset{\|}{C}}$CH=CH—CH=CHCH$_3$]$^+$, 95

[—COCH=CH—CH—CHCH$_3$]$^+$ and 67

[—CH=CH—CH=CHCH$_3$ ]$^+$

Infrared absorption spectrum ($\nu$cm.$^{-1}$): 3100 to 2850 (aromatic alkyl $\nu$C—H), 1745, 1710 (ester $\nu$C=O) and 1655 (olefinic $\nu$C=C).

EXAMPLE 15

[2-(Acetoxy)ethyl 2-(2-fluoro-4-biphenylyl)propionate (Compound No. 8)]

In 35 ml. of anhydrous pyridine was dissolved 7.55 g. (26.2 mmoles) of 2-hydroxyethyl-2-(2-fluoro-4-biphenylyl)propionate. To the resulting solution was added dropwise 4 g. (39.3 mmoles) of acetic anhydride with ice-cooling. After completion of the addition, the resulting reaction mixture was stirred at 40° C. for 3 hours, and then cooled. The reaction mixture was poured into water added with ice and extracted with 400 ml. of diethyl ether. The resulting extract was washed successively with 10% hydrochloride and water, and the organic layer was dried with anhydrous magnesium sulfate. After distilling away the solvent under reduced pressure, the obtained clear oily material was distilled under reduced pressure for purification to give 7.61 g. (yield: 88%) of the desired compound being a clear oily material.

The physicochemical properties of the obtained compound were consistent with those obtained in Example 9.

EXAMPLE 16

[2-(Acetoxy)ethyl 2-(2-fluoro-4-biphenylyl)propionate (Compound No. 8)]

To 100 ml. of anhydrous acetonitrile were added 2.82 g. (10 mmoles) of potassium salt of FP, 0.1 g. of 18-crown-6 and 1.22 g. (10 mmoles) of 2-acetoxyethyl chloride, and the reaction mixture was stirred at a room temperature for 8 hours. The resulting reaction mixture was treated by a conventional method and purified in the same manner as in example 9 to give 1.48 g. (yield: 44.8%) of the desired compound being a clear oily material.

The physicochemical properties of the obtained compound were consistent with those obtained in Example 9.

EXAMPLE 17

[2-(Propionyloxy)ethyl 2-(2-fluoro-4-biphenylyl)propionate (Compound No. 9)]

To 100 ml. of anhydrous acetonitrile were added 2.82 g. (10 mmoles) of potassium salt of FP, 1.4 g. (10 mmoles) of 2-propionyloxyethyl chloride, 1 g. of triethylamine and 1.6 g. of potassium iodide, and then the reaction mixture was stirred at 60° C. for 5 hours. The resulting reaction mixture was post-treated by a conventional method, and distilled under reduced pressure for purification to give 2.86 g. (yield: 83%) of the desired compound being a clear oily material.

The physicochemical properties of the obtained compound were consistent with those obtained in Example 10.

EXAMPLE 18

[Tablet]

To 100 mg. of 2-(acetoxy)ethyl 2-(2-fluoro-4-biphenylyl)propionate was added 30 mg. of Aerosil (registered trademark, made by Japan Aerosil Co., Ltd.), and the mixture was pulverized. To the resulting powder were added 35 mg. of dibasic calcium phosphate anhydrous, 45 mg. of Avicel (registered trademark, made by Asahi Kasei Co., Ltd.), 6 mg. of ECG 505 (carboxymethyl cellulose calcium salt made by Nichirin Chemical Industry Co., Ltd.) and 4 mg. of calcium stearate, and then the mixture was blended and compressed to give a tablet.

EXAMPLE 19

[Suppository]

A mixture of 1240 mg. of Witepsol H-15 (mixture of triglyceride and monoglyceride made by Dinamit Novel Co., Ltd., Witepsol: registered trademark) and 310 mg. of Witepsol E-85 (made by Dinamit Novel Co., Ltd.) was melted at 60° to 70° C. After cooling the mixture to a temperature of 45° C., 150 mg. of 2-(acetoxy)ethyl 2-(2-fluoro-4-biphenylyl)propionate was added thereto. The resulting mixture was stirred until it became homogeneous, and then 1.7 g. thereof was injected in a container of 1.9 ml. at 40° C. to make solid with cooling.

EXAMPLE 20

[Soft gelatin capsule]

(a) For oral administration

In 100 mg. of PEG 400 (polyethyleneglycol) was dissolved 100 mg. of 2-(acetoxy)ethyl 2-(2-fluoro-4-biphenylyl)propionate, and then 200 mg. of the resulting solution was filled up in a soft gelatin capsule (made by R. P. Scherer Co., Ltd.; size: 3 to 2 round A). (b) For Suppositories In 260 mg. of PEG 400 was dissolved 150 mg. of 2-(acetoxy)ethyl 2-(2-fluoro-4-biphenylyl)propionate, and then 410 mg. of the resulting solution was filled up in a soft gelatin capsule (made by R. P. Scherer Co., Ltd.; size: 85 to 86 suppository A).

EXAMPLE 31

[Cream]

According to the following formulation, a 1% gel cream was prepared as follows:

| | |
|---|---|
| 2-(Acetoxy)ethyl 2-(2-fluoro-4-biphenylyl) propionate | 10 g. |
| Myristin isopropyl (made by Nikko Chemicals Co., Ltd.) | 100 g. |
| Ethanol | 50 g. |
| Polyoxyethylene monostearate | 10 g. |
| Carboxyvinyl polymer-940 | 15 g. |
| Coconut oil (fatty acid diethanol amide) | 30 g. |
| Distilled water | Sufficient amount |
| | Total 1000 g. |

In myristin isopropyl wws dissolved 2-(acetoxy)ethyl 2-(2-fluoro-4-biphenylyl)propionate. To the resulting solution were added ethanol, carboxyvinyl polymer-940 swelled in 500 ml. of water and polyoxyethylene dissolved in 100 ml. of water, and then the resulting mixture was throughly stirred until it became homogeneous. To the homogeneous mixture were added coconut oil blended in 100 ml. of water and sufficient amount of distilled water, and then the resulting mixture was throughly stirred until it became homogeneous.

EXAMPLE 22

[Inhibitory effect on carrageenan-induced edema]

With respect to the present FP derivatives (Compound Nos. 1 to 13), there was tested inhibitory effect on carrageenan-induced edema.

Five Wistar male rats weighing about 150 g. were used as one group. A 1% dispersion of carrageenan was injected intracutaneously into the foot pad of the right hind foot in a dose of 0.1 ml./rat. The compounds to be tested were orally administered to the rats fasted for 15 hours one hour before the carrageenan injection, or intravenously administered 2 hours after the carrageenan injection. The volume of the foot subjected to the injection was measured by a mercury plethysmography 3 hours after the carrageenan injection on the test by oral route or 2 hours after the carrageenan injection on the test by intravenous route, and the carrageenan-induced edema was estimated from the obtained measurements. The results are shown in Table 2.

TABLE 2

| | Compound No. | $ED_{50}$ mg./kg. | |
|---|---|---|---|
| | | p.o. | i.v. |
| Compounds of the invention | 1 | 0.5 | 0.08 |
| | 2 | 0.5 | 0.07 |
| | 3 | 0.6 | 0.10 |
| | 4 | 0.6 | 0.08 |
| | 5 | 0.5 | 0.06 |
| | 6 | 1.5 | 0.50 |
| | 7 | 0.6 | 0.10 |
| | 8 | 0.7 | — |
| | 9 | 0.7 | — |
| | 10 | 0.9 | — |
| | 11 | 1.0 | — |
| | 12 | 0.9 | — |
| | 13 | 0.9 | — |
| Comparative | acemethacin | 8.3 | — |

TABLE 2-continued

| | Compound No. | $ED_{50}$ mg./kg. | |
|---|---|---|---|
| | | p.o. | i.v. |
| compounds | indomethacin | 5.5 | 1.25 |
| | FP | 0.8 | 0.3 |

EXAMPLE 23

[Gastric ulceration]

With respect to the present FP derivatives (Compound Nos. 1 to 13), there was tested gastric ulceration.

Five Wistar male rats weighing about 150 g. were used as one group. The rats were fasted for 24 hours before the test.

Six hours after orally administration of the present compounds to be tested, there was observed an existence of gastric ulcer by the method of Okabe et al (Ohyoyakuri, 16, 241 to 247 (1978)). The $UD_{50}$ values were calculated from the ulcer incidence of gastric ulcer by the method of Litchfield-Wilcoxon. The results are shown in Table 3.

TABLE 3

| | Compound No. | $UD_{50}$ mg./kg. |
|---|---|---|
| Compounds of the invention | 1 | 3.6 |
| | 2 | 2.5 |
| | 3 | 2.0 |
| | 4 | 2.0 |
| | 5 | 2.0 |
| | 6 | 5.0 |
| | 7 | 2.5 |
| | 8 | 2.0 |
| | 9 | 2.0 |
| | 10 | 3.0 |
| | 11 | 3.0 |
| | 12 | 3.0 |
| | 13 | 3.0 |
| Comparative compounds | acemethacin | 17.5 |
| | indomethacin | 5.0 |
| | FP | 1.0 |

EXAMPLE 24

[Hydrolysis of FP derivatives in plasma]

With respect to the present FP derivatives (Compound Nos. 1 to 13), there was tested the hydrolyzing rate in human plasma or rat plasma.

The compounds to be tested (Compound Nos. 1 to 7) and the compounds to be tested (Compound Nos. 8 to 13) were, respectively, added to 1 ml. of human plasma and 1 ml. of rat plasma, in an amount corresponding to 50 μg. of FP. Each reaction mixture was incubated at 37° C. for one hour.

The free FP formed by esterase in the plasma was extracted with benzene. After treating the extract with N,O-bis(trimethylsilylacetamide) for trimethylsilylation, the obtained material was determined by gas-liquid chromatography. The results are shown in Table 4.

TABLE 4

| | Compound No. | Hydrolyzing rate (%) |
|---|---|---|
| Compounds of the invention | 1 | 97.5 |
| | 2 | 94.6 |
| | 3 | 86.3 |
| | 4 | 81.4 |
| | 5 | 114.8 |

TABLE 4-continued

|  | Compound No. | Hydrolyzing rate (%) |
|---|---|---|
|  | 6 | 3.8 |
|  | 7 | 70.3 |
|  | 8 | 100.9 |
|  | 9 | 98.9 |
|  | 10 | 99.5 |
|  | 11 | 99.8 |
|  | 12 | 100.3 |
|  | 13 | 101.0 |
| Comparative compounds | acemethacin | 4.2 |
|  | indomethacin | — |
|  | FP | — |

EXAMPLE 25

[Acute toxicity]

Eight male SLC-ddY mice 5 week old weighing 25 to 30 g. were used as one group. The compound to be tested was orally administered using a stomach tube. The animals were kept under observation for 2 weeks. The numbers of dead animals were counted and the $LD_{50}$ values were calculated by the method of Litchfield Wilcoxon. The results are shown in Table 5.

TABLE 5

|  | Compound No. | $LD_{50}$ mg./kg. |
|---|---|---|
| Compounds of the invention | 1 | 880 |
|  | 2 | 750 |
|  | 3 | 600 |
|  | 4 | 600 |
|  | 5 | 900 |
|  | 6 | >1000 |
|  | 7 | 840 |
|  | 8 | 650 |
|  | 9 | 700 |
|  | 10 | 800 |
|  | 11 | 880 |
|  | 12 | 750 |
|  | 13 | 750 |
| Comparative compounds | acemethacin | 18.0 |
|  | indomethacin | 14.0 |
|  | FP | 440 |

What we claim is:

1. A biphenylylpropionic acid ester derivative having the formula (I):

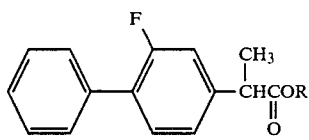
(I)

wherein R is an alkylcarbonyloxyalkyl group or an alkenylcarbonyloxyalkyl group having the formula (II):

$$-CH_2-(CH_2)_m-O\overset{O}{\overset{\|}{C}}R^1 \quad (II)$$

wherein $R^1$ is an alkyl group having 1 to 15 carbon atoms or an alkenyl group having 2 to 8 carbon atoms and m is 0 or an integer of 1.

2. The biphenylylpropionic acid derivative of claim 1, wherein R is acetoxymethyl, propionyloxymethyl, isobutyryloxymethyl, pivaloyloxymethyl, palmitoyloxymethyl, crotonoyloxymethyl, 3,3-dimethylacryloyloxymethyl, 2-acetoxyethyl, 2-propionyloxyethyl, 2-crotonoyloxyethyl, 2-(3,3-dimethylacryloyloxy)ethyl, 2-(2,4-hexadienoyloxy)ethyl or 2-(3,7-dimethyl-2,6-octadienoyloxy)ethyl.

3. A pharmaceutical composition having an anti-inflammatory, analgesic and antipyretic activity, which comprises, as the effective ingredient, an amount effective to provide an anti-inflammatory, analgesic or antipyretic activity, of a biphenylylpropionic acid derivative having the formula (I):

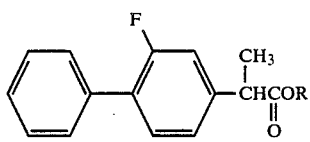
(I)

wherein R is an alkylcarbonyloxyalkyl group or an alkenylcarbonyloxyalkyl group having the formula (II):

$$-CH_2-(CH_2)_m-O\overset{O}{\overset{\|}{C}}R^1 \quad (II)$$

wherein $R^1$ is an alkyl group having 1 to 15 carbon atoms or an alkenyl group having 2 to 8 carbon atoms and m is 0 or an integer of 1, and a pharmaceutically acceptable carrier.

4. The pharmaceutical composition of claim 3 wherein R is acetoxymethyl, propionyloxymethyl, isobutyryloxymethyl, pivaloyloxymethyl, palmitoyloxymethyl, crotonoyloxymethyl, 3,3-dimethylacryloyloxymethyl, 2-acetoxyethyl, 2-propionyloxyethyl, 2-crotonoyloxyethyl, 2-(3,3-dimethylacryloyloxy)ethyl, 2-(2,4-hexadienoyloxy)ethyl or 2-(3,7-dimethyl-2,6-octadienoyloxy)ethyl.

5. The pharmaceutical composition of claim 3, which is in a preparation form of tablet, capsule, suppository and cream.

* * * * *